US007939034B2

(12) United States Patent
Shiraishi et al.

(10) Patent No.: US 7,939,034 B2

(45) Date of Patent: May 10, 2011

(54) METHOD AND TOOL FOR COLLECTING BLOOD PLASMA

(75) Inventors: Fumiko Shiraishi, Ashigara-kami-gun (JP); Yasunori Ichikawa, Ashigara-kami-gun (JP); Takayuki Fujiwara, Minami-ashigara (JP); Hideharu Nagasawa, Ashigara-kami-gun (JP); Kazunori Takahashi, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 741 days.

(21) Appl. No.: 11/905,026

(22) Filed: Sep. 27, 2007

(65) Prior Publication Data

US 2008/0073297 A1 Mar. 27, 2008

(30) Foreign Application Priority Data

Sep. 27, 2006 (JP) ................................ 2006-263485

(51) Int. Cl.
*C12M 1/12* (2006.01)

(52) U.S. Cl. ......................... 422/513; 422/502; 436/177

(58) Field of Classification Search ......................... None
See application file for complete search history.

(56) References Cited

U.S. PATENT DOCUMENTS

| | | | | |
|---|---|---|---|---|
| 7,223,364 | B1 * | 5/2007 | Johnston et al. | 422/68.1 |
| 2003/0175167 | A1 | 9/2003 | Takanori et al. | |

FOREIGN PATENT DOCUMENTS

| | | | |
|---|---|---|---|
| EP | 1 346 773 | A2 | 9/2003 |
| JP | 2000-171461 | A | 6/2000 |
| JP | 2003-83958 | A | 3/2003 |
| JP | 2003-270239 | A | 9/2003 |
| JP | 2005-292092 | A | 10/2005 |
| JP | 2006-52950 | A | 2/2006 |
| WO | WO 03008931 | A2 * | 1/2003 |
| WO | 2005/089082 | A2 | 9/2005 |

OTHER PUBLICATIONS

Notice of Reasons for Rejection, dated Dec. 14, 2010, issued in corresponding JP Application No. 2006-263485, 4 pages in English and Japanese.

* cited by examiner

*Primary Examiner* — Yelena G Gakh
*Assistant Examiner* — Christopher A Hixson
(74) *Attorney, Agent, or Firm* — Sughrue Mion, PLLC

(57) ABSTRACT

According to a blood plasma collection tool of the present invention, a phenomenon that blood cells in blood spontaneously precipitate due to an effect of gravitational force takes place in the very narrow microspace (separation part) having the very narrow depth in the direction of gravitational force of not greater than 1 mm, and the overflow channel functions as a dam against the separation part so that the blood plasma separated out as supernatant fluid can overflow beyond the overflow channel, whereby the blood cells separated out can be prevented from entering the collection part. Therefore, blood plasma can be collected by accurately and readily separating blood plasma and blood cells in a small amount of blood from each other in a short time, using a small tool having a simple structure.

17 Claims, 11 Drawing Sheets

14A

METHOD AND TOOL FOR COLLECTING BLOOD PLASMA

BACKGROUND OF THE INVENTION

1. Field of the Invention

The present invention relates to a method and tool for collecting blood plasma, and particularly to a technology for effectively collecting only blood plasma by separating blood plasma and blood cells (red blood cells, white blood cells, blood platelets) in blood from each other in a short time before a blood test.

2. Description of the Related Art

When a blood test is conducted, blood of several mL is collected depending on measurement items by a vacuum blood collecting tube and the vacuum blood collecting tube is set up on various automatic analyzers. The automatic analyzers are large and some hospitals may sometimes ask a test center to inspect blood because of no possession of test equipment. Therefore, it is the present situation that it takes a time to obtain the inspection result. When an emergency clinic test is conducted, it is required to go to facilities having test equipment, so that the test itself is a physical load to old people and the sick. Further, if the environment allowing a blood test to be conducted more readily and more frequently is prepared, protective measures against illness may be enhanced and the quality of life may be improved.

Now, blood used for a blood test may be frequently analyzed optically, and it is known that a solid body in blood, for example, hemoglobin in red blood cells, especially its own color prevents colorimetric measurement. Therefore, in order to provide an accurate test result, as pretreatment for a blood test, it is necessary to prepare a specimen only composed of blood plasma (including serum) obtained by separating blood cells from blood. For this purpose, in order to readily collect only blood plasma by separating to remove blood cells from blood at the site where a blood test is conducted, not limited to a big hospital or a test center equipped with a large blood plasma collection system, the blood plasma collection system has to be made smaller to be a simple test instrument and a blood plasma collection method is required to be made simpler. Further, to mitigate a physical and psychological impact of a patient undergoing a blood test, it is necessary to test by a small amount of blood collected.

In such circumstances, the following items are required for a blood plasma collection method and tool.

(1) Blood plasma collection has to be simple using a small tool and an operation for collection of a small amount of blood. For example, in order to readily implement collection of blood and to allow test to be conducted by anyone anywhere, an amount of blood collected has to be reduced to the degree of several dozens μL at the most, which may be collected by a lancet.

(2) A time necessary to collect blood plasma, that is, a separation time for separating blood plasma and blood cells from each other has to be shortened as much as possible, because fresh blood changes as time passes and becomes unusable for test.

(3) Medicines such as a separation agent do not have to be used, because they may degrade test accuracy.

For these items, there are the following systems as a conventional blood plasma collection system or tool.

Japanese Patent Application Laid-Open No. 2003-83958 discloses a method for separating blood plasma and blood cells from each other by the centrifugal separation method, and the method has a problem of a long separation time, as well as an additional operation for putting blood plasma into a blood test device after separating out blood cells. Japanese Patent Application Laid-Open No. 2006-52950 discloses improvement in size of a device which, based on the centrifugal separation method, was made large, and proposes a method that blood is introduced into a microchip and the microchip is entirely run by a centrifugal separator, but miniaturization of the device is restricted by necessity of a high speed rotating part.

Japanese Patent Application Laid-Open No. 2003-270239 discloses a method for separating blood plasma and blood cells from each other by the membrane separation method, and the method can collect a very small amount of blood to separate, but to implement this method, dilution of the collected blood or extraction of blood plasma to be tested from a small container is required, resulting in complicated operation. Further, because a membrane, used for the membrane separation method, itself has water holding capacity, a part of a specimen may be readily damaged, moreover because it is necessary to push out blood into a filter by pressurization, unfortunately the filter may clog or hemolysis may occur.

Japanese Patent Application Laid-Open No. 2000-171461 discloses a method except the centrifugal separation method and the membrane separation method, in which, by alternately laying cation exchange material and anion exchange material one on the other on a surface of a substrate for introducing blood, the surface of the substrate is made to be charged with cations, and then red blood cells (a sort of blood cells) charged with anions are captured electrically on the surface of the substrate. However, this method has a problem of troublesome coating, as well as quite conceivable, electrostatic attachment of components in blood plasma.

Further, Japanese Patent Application Laid-Open No. 2005-292092 also discloses a method except the centrifugal separation method and the membrane separation method, in which solid components and liquid components in blood are separated from each other by adding flocculant (separation assistant) to a small amount of blood to generate aggregate and precipitating out the aggregate through a channel structure. However, this method has a problem that the channel has a complex shape and it takes a time to effect agglutination, moreover the flocculent may have a bad influence on a blood test.

Further, conventionally, blood plasma having blood cells separated out is generally inspected at another place, which is a time loss, and also a specimen loss. Therefore, desired is a method by which separation of blood cells and a blood test can be conducted concurrently at the same place.

SUMMARY OF THE INVENTION

However, as described above, the conventional blood plasma collection method and device have merits and demerits, and cannot meet the requirements according to the items (1) to (3) described above.

The present invention was made in view of these circumstances, and an object of the present invention is to provide a blood plasma collection method by which blood plasma can be collected by accurately, readily separating blood plasma and blood cells in a small amount of blood from each other in a short time, using a small tool having a simple structure, and the tool.

A first aspect of the present invention, to achieve the object described above, provides a blood plasma collection tool including: a separation part for separating blood cells from blood due to spontaneous sedimentation; a collection part for collecting blood plasma obtained by separating out blood cells in the separation part as supernatant fluid; and an overflow channel for overflowing the blood plasma separated out in the separation part to the collection part, in which the separation part is a long microspace having a depth in the direction of gravitational force of not greater than 1 mm.

According to the first aspect, a phenomenon that blood cells in blood spontaneously precipitate due to an effect of gravitational force takes place in the very narrow microspace (separation part) having the very narrow depth in the direction of gravitational force of not greater than 1 mm, and the overflow channel functions as a dam against the separation part so that the blood plasma separated out as supernatant fluid can overflow beyond the overflow channel, whereby the blood cells separated out can be prevented from entering the collection part. Therefore, blood plasma can be collected by accurately and readily separating blood plasma and blood cells in a small amount of blood from each other in a short time, using a small tool having a simple structure.

A second aspect of the present invention is according to the first aspect, in which let H (m) be the depth of the separation part in the direction of gravitational force, L (m) be a length of the separation part in the flow direction of the blood, and Hb (m) be a sedimentation distance in which the blood cells can precipitate while the blood passes through the length (L) of the separation part, then it is the condition that a height h (m) of a bottom surface of the overflow channel relative to a bottom surface of the separation part is made to meet the following items (A) or (B):

(A) When $Hb \geqq H$, $h \geqq 2\times10^{-5}$.

(B) When $Hb<H$, $h \geqq H-Hb$.

According to the second aspect, the height h of the bottom surface of the overflow channel relative to the bottom surface of the separation part is set to meet the conditions (A), (B), so that blood cells separated out due to spontaneous sedimentation can be prevented from entering the collection part, and therefore, blood plasma can be collected accurately.

A third aspect of the present invention is according to the first or second aspect, in which a dam is provided in the overflow channel.

According to the third aspect, blood cells which could not be separated out in the separation part can be separated out before the collection part by the dam provided in the overflow channel, and therefore blood plasma can be collected with small contamination of blood cells.

A fourth aspect of the present invention is according to any one of the first to third aspects, in which a filter is provided in the overflow channel.

According to the fourth aspect, blood cells which could not be separated out even in the separation part can be unfailingly separated out before the collection part by the filter provided in the overflow channel, and therefore blood plasma can be collected with very small contamination of blood cells. Further, blood from which most of blood cells were separated in the separation part is passed through the filter, and therefore it is difficult for the filter to be clogged.

A fifth aspect of the present invention is according to any one of the first to fourth aspects, in which a plurality of the separation parts are provided in series.

According to the fifth aspect, blood cells which could not be separated even in the separation part can be unfailingly separated before the collection part, and therefore blood plasma can be collected with small contamination of blood cells.

A sixth aspect of the present invention is according to any one of the first to fifth aspects, in which an inlet of the separation part is formed in the central part of a side wall face of the separation part in the depth direction.

According to the sixth aspect, a distance between an interface of blood introduced into the separation part and an upper surface of the separation part becomes equal to a distance between the interface of blood and a bottom surface of the separation part. Accordingly, when blood is introduced into the separation part, the blood can be prevented from covering only one of the upper surface and the bottom surface of the separation part and spreading. Therefore, it becomes easy to push out blood in the separation part to flow, whereby accurate separation of blood plasma from blood can be provided.

A seventh aspect of the present invention is according to any one of the first to sixth aspects, in which a cross section shape of a bottom of the separation part on a cross section in the width direction of the blood flow is of V-shaped type whose depth increases from both ends toward the central portion.

According to the seventh aspect, blood cells separated out can be stably captured, and therefore the blood cells can be prevented from reentering blood plasma.

An eighth aspect of the present invention is according to any one of the first to seventh aspects, in which side wall faces of the separation part on the side of the inlet and (or) an outlet on a cross section along the flow direction of the blood are inclined to the direction of gravitational force and the angle of inclination is smaller than 90°.

According to the eighth aspect, the side wall faces of the separation part on the side of the inlet and (or) the outlet are inclined to the direction of gravitational force, and therefore a separation rate of blood cells can be enhanced by a boycott effect. Moreover, blood cells can be prevented from entering the collection part of blood plasma by generating a flow in the direction opposite to the direction of the blood flow.

A ninth aspect of the present invention, to achieve the object described above, provides a blood plasma collection method including the steps of: separating blood cells from blood due to spontaneous sedimentation; and collecting blood plasma obtained as supernatant fluid by separating out blood cells in the step of separating, in which the blood is made to flow in laminar flow from the step of separating to the step of collecting.

A tenth aspect of the present invention is according to the ninth aspect, in which the blood cells are separated out by making the blood to flow in a microspace having a depth in the direction of gravitational force of not greater than 1 mm in the step of separating.

According to the present invention, blood plasma can be collected by accurately, readily separating blood plasma and blood cells in a small amount of blood from each other in a short time using a small tool having a simple structure.

DETAILED DESCRIPTION OF THE PREFERRED EMBODIMENTS

Now, preferred embodiments of a blood plasma collection method and tool according to the present invention will be hereinafter described with reference to the accompanying drawings.

First, one example of an embodiment according to the present invention will be described. A blood plasma collection method of the present embodiment is a method for separating blood plasma and blood cells from each other due to spontaneous sedimentation in a short time, using a blood plasma collection tool in which a very narrow microspace having a depth in the direction of gravitational force of not greater than 1 mm is formed. In addition, blood used for the present invention is not limited to human blood, but may be blood of various animals.

Figures 1A, 1B:
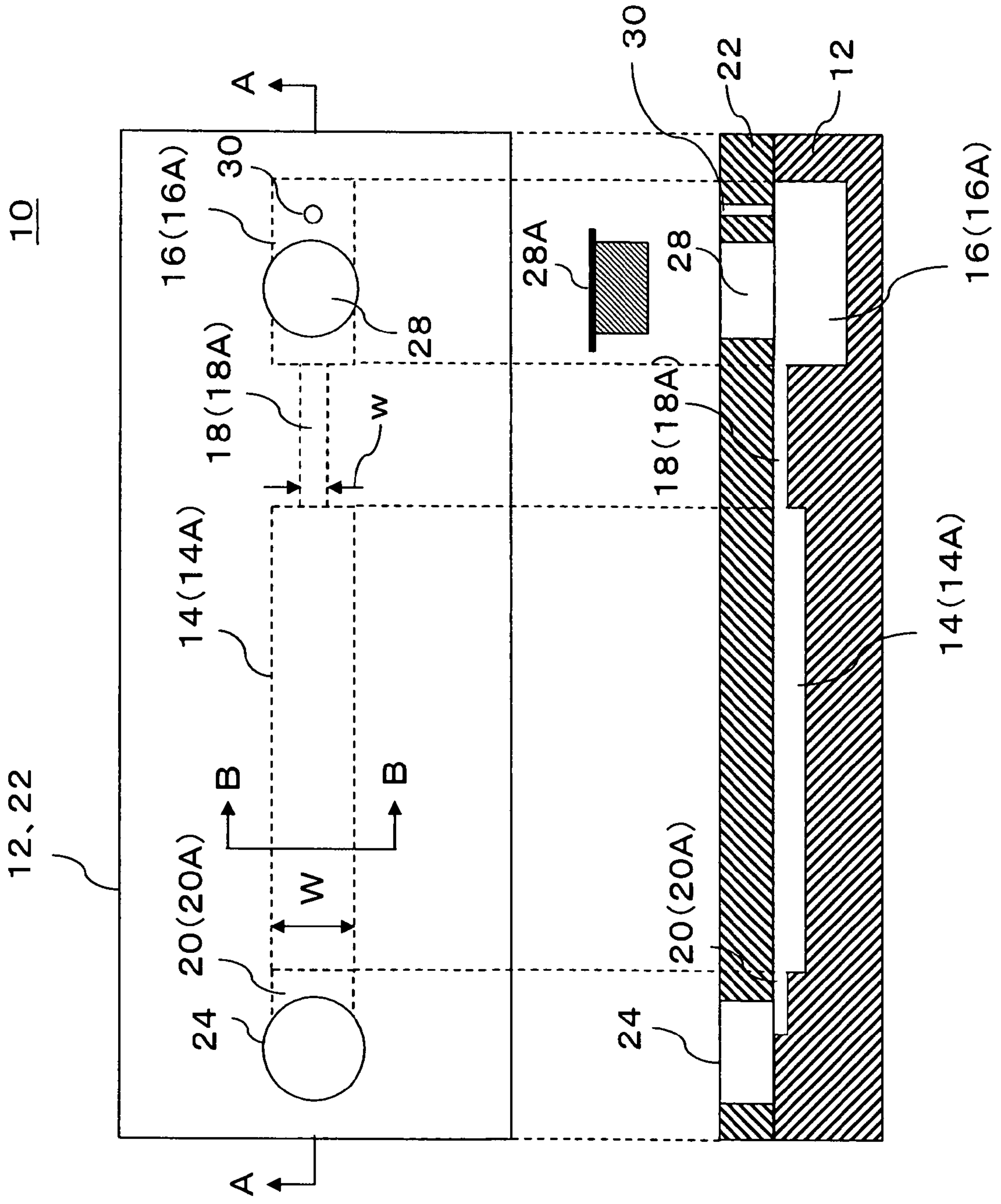
FIGS. 1A and 1B are schematic views for describing a rough configuration of a blood plasma collection tool according to the present invention.
Figure 2:
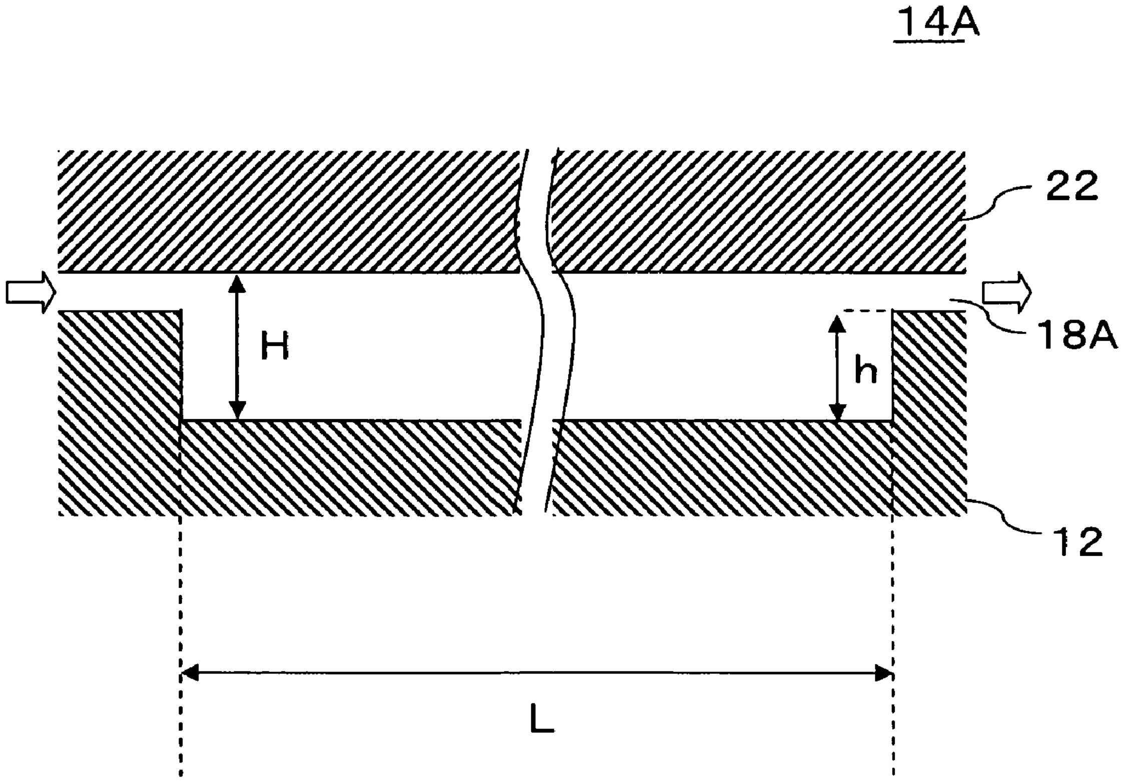
FIG. 2 is a partial, enlarged cross-sectional view of a separation part of FIGS. 1A and 1B.

FIGS. 1A and 1B are schematic views for describing a rough configuration of a blood plasma collection tool 10 according to the present invention. As for these, FIG. 1A is a top view of the blood plasma collection tool 10, and FIG. 1B is a cross-sectional view of the blood plasma collection tool 10 taken along the line A-A. FIG. 2 is a partial, enlarged cross-sectional view of a separation part 14A of FIG. 1B. Now, an upstream portion and a downstream portion are hereinafter defined relative to the direction of blood flow (the direction along the line A-A) on a basis.

As shown in FIGS. 1A and 1B, the blood plasma collection tool 10 mainly includes: a substrate 12 in which a first concave portion 14 having a depth of not greater than 1 mm, a second concave portion 16 and a third concave portion 18 for communicating the first concave portion 14 with the second concave portion 16 are formed on a surface of a plate-like body; and a cover plate 22 tightly fixed on a surface of the substrate 12 for covering the first to third concave portions 14, 16, 18 to form one microchannel on the substrate 12. Spaces formed by covering the first concave portion 14, the second concave portion 16 and the third concave portion 18 formed on the surface of the substrate 12 with the cover plate 22 are called "separation part 14A", "collection part 16A" and "overflow channel 18A", respectively.

The separation part 14A is a narrow, long microspace having a depth in the direction of gravitational force of not greater than 1 mm. Further, on the downstream side of the separation part 14A, the collection part 16A is formed. Then, a downstream end of the separation part 14A and an upstream end of the collection part 16A are communicated with each other by the overflow channel 18A. This overflow channel 18A functions as a dam for partially isolating the collection part 16A from the separation part 14A.

Further, an upstream end of the separation part 14A is in communication with a flow channel 20A in communication with a fluid storage 24 which is a columnar, hollow portion formed in the cover plate 22. Further, in a part of the cover plate 22 corresponding to the collection part 16A, a collection port 28 for externally collecting blood plasma collected in the collection part 16A and an air vent 30 for communicating the inside of the collection part 16A with the outside air are formed. The collection port 28 is adapted to fit to a tight seal member 28A.

As shown in FIG. 2, the depth H of the separation part 14A in the direction of gravitational force is set to be small enough to separate out blood cells in a short time and in a range so that blocking due to blood cells which precipitated can be prevented. For this purpose, the depth H of the separation part 14A is preferably not smaller than 0.02 mm and not greater than 1 mm, and more preferably not smaller than 0.1 mm and not greater than 0.5 mm.

A width W of the separation part 14A in the horizontal direction (see FIGS. 1A and 1B) is preferably not smaller than 0.02 mm and not greater than 20 mm, and more preferably not smaller than 0.1 mm and not greater than 10 mm, taking into consideration prevention of blocking by blood cells and wettability of blood (easiness of making wet and spreading).

A length L of the separation part 14A in the flow direction is preferably not smaller than 1 mm and not greater than 200 mm, more preferably not smaller than 1 mm and not greater than 50 mm, and further more preferably not smaller than 1 mm and not greater than 25 mm, taking into consideration easiness of handling of the blood plasma collection tool.

A volume of the separation part 14A is set so that there is enough room to contain blood cells which precipitated due to separation without blocking of the flow channel. A hematocrit value of blood (ratio of a volume of red blood cells contained in a constant amount of blood), though there are individual differences, is approximately to the degree from 33 to 55%. If the volume of the separation part 14A is smaller than an amount of blood to be processed (blood throughput), the volume of the separation part 14A is set to be not smaller than 33 to 55% of the blood throughput. Further, the volume of the separation part 14A may be set to be a volume able to contain the blood throughput. Therefore, the volume of the separation part 14A is preferably not smaller than 0.5 μL and not greater than 50 μL, and more preferably not smaller than 0.5 μL and not greater than 10 μL.

Figure 3A:
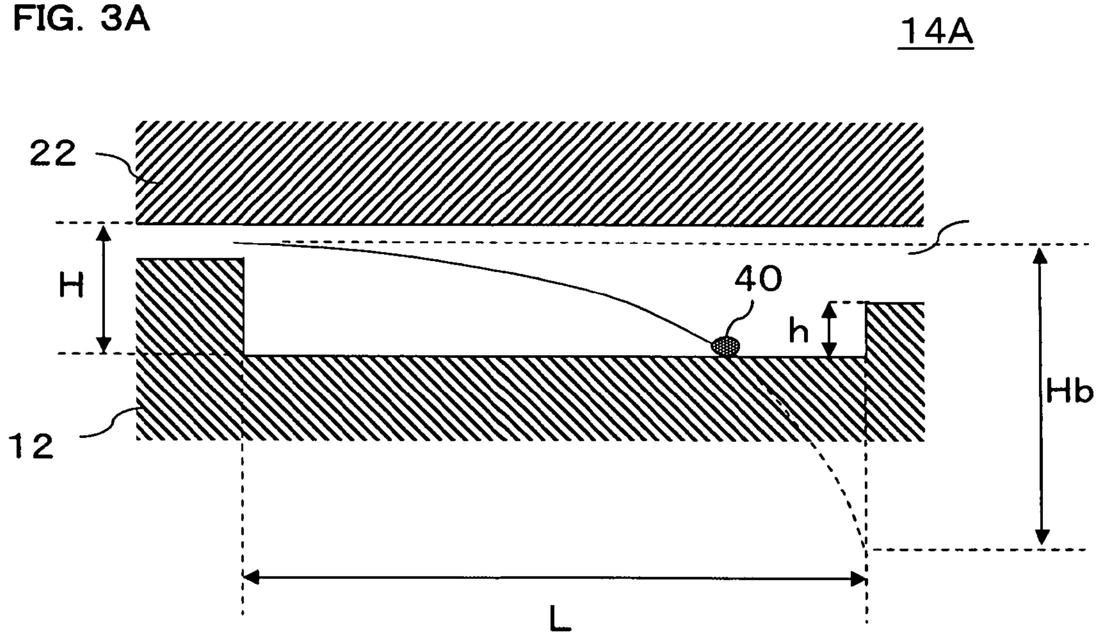
FIGS. 3A and 3B are schematic views for describing relation between a sedimentation distance in the separation part of FIGS. 1A and 1B and a height of a dam.
Figure 3B:
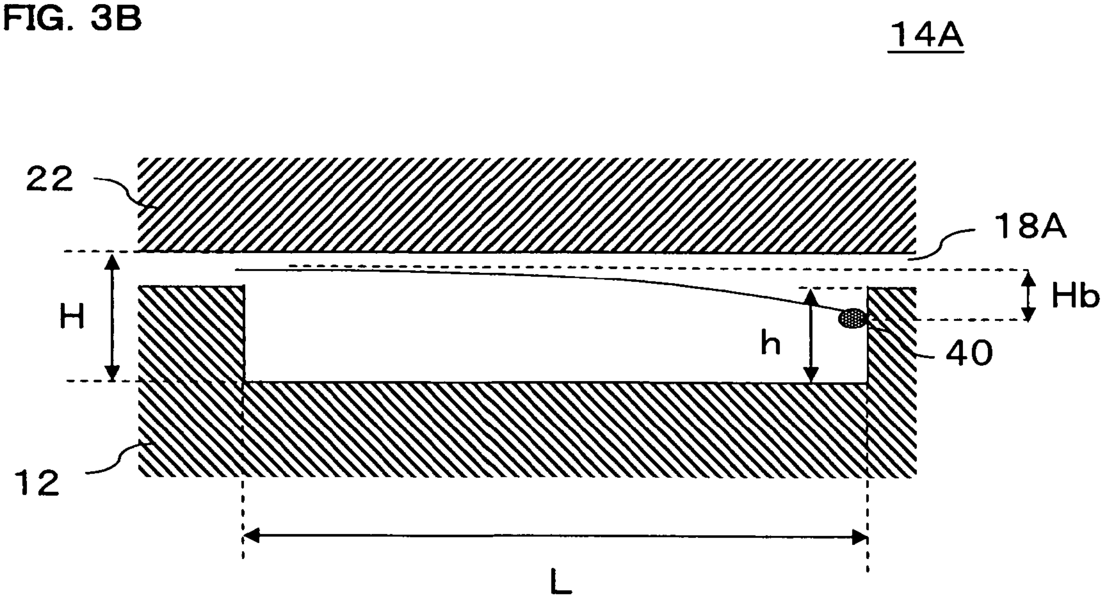

In order to prevent blood cells which spontaneously precipitated in the separation part 14A from reentering the collection part 16A, a height h from the bottom surface of the separation part 14A to a bottom surface of the overflow channel 18A (hereinafter, simply called "height h of the overflow channel 18A") is set as follows. FIGS. 3A and 3B are schematic views for describing relation between a distance to which blood cells in blood can precipitate while the blood flows in the separation part 14A (hereinafter, called "sedimentation distance Hb of blood cells") and the height h of the overflow channel 18A.

A sedimentation rate vb (m/sec) of blood cells (in the direction of gravitational force) may be expressed by the following expression (1):

$$vb=(2/9)\cdot\{(\rho 1-\rho 2)\cdot g\cdot r^2/\eta\} \quad (1)$$

{vb: sedimentation rate of blood cells (m/sec), ρ1: density of blood cells (kg/m$^3$), ρ2: density of fluid (blood plasma) (kg/m$^3$), g: gravitational acceleration (m/sec$^2$), r: radius, supposing that a blood cell is spherical (m), η: viscosity of fluid (blood plasma) (kg/(m·sec))}

An initial rate vo at which blood flows into the separation part 14A (average flow rate of components in the horizontal direction) may be expressed by the following expression (2), where a supply flow rate of blood is Q (m$^3$/sec):

$$vo=Q/(H\cdot W) \quad (2)$$

Therefore, a sedimentation time of blood cells t (sec) in the separation part 14A may be expressed by t=L/vo. Then, the sedimentation distance Hb (m) of blood cells of blood in the separation part 14A may be expressed by the following expression (3):

$$Hb=vb\cdot L/vo \quad (3)$$

Then, when $Hb \geqq H$, as shown in FIG. 3A, because a blood cell 40 precipitates down to the bottom of the separation part 14A within the range of the length L in the horizontal direction, the height h of the overflow channel 18A is set to be a height able to contain blood cells, that is, a height of not smaller than 0.02 mm.

On the contrary, when $Hb<H$, as shown in FIG. 3B, because the blood cell 40 does not precipitate down to the bottom of the separation part 14A within the range of the length L in the horizontal direction, the height h of the overflow channel 18A is set to be a height sufficient to capture the blood cell 40. In this case, the height h of the overflow channel 18A is set to be $h \geqq H-Hb$.

Figure 4:
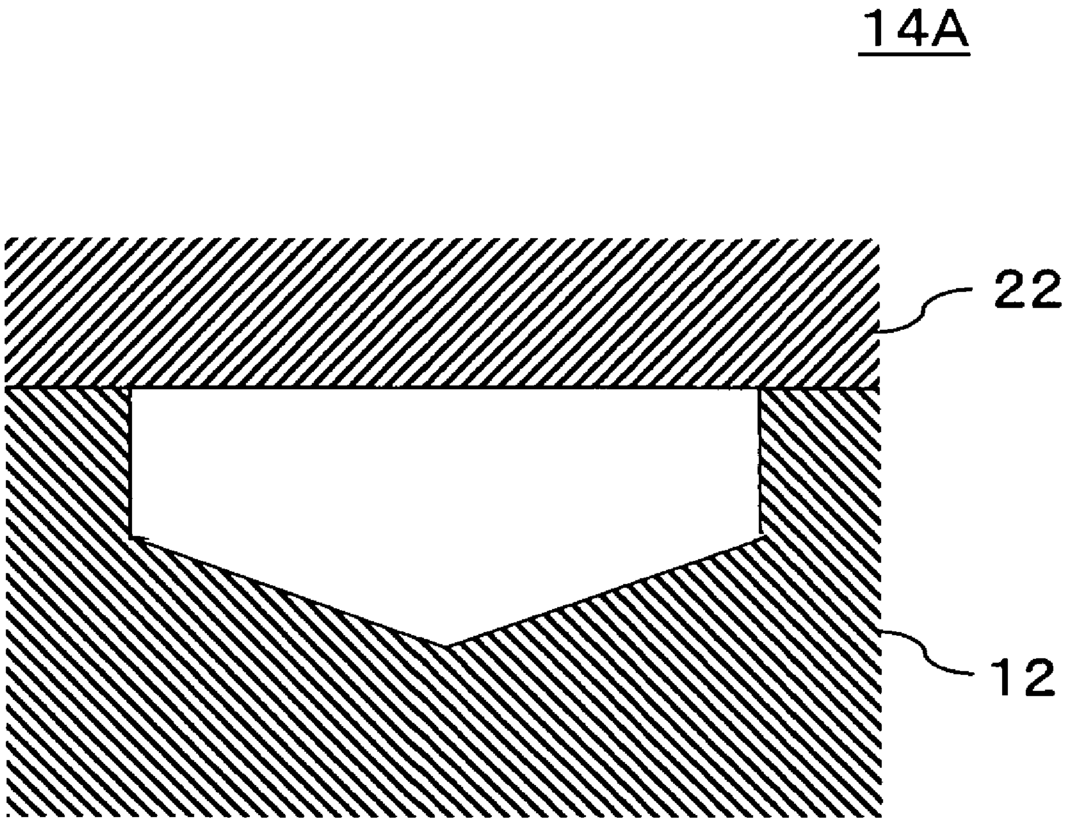
FIG. 4 is a cross-sectional view illustrating a variation of the separation part.

Cross section shapes of the separation part 14A, the collection part 16A, the overflow channel 18A and the flow channel 20A taken along the direction of the line B-B are not especially restricted, and various shapes such as a rectangle (square, oblong), a trapezoid, a V shape and a semicircle may be used. Especially for the separation part 14A, because of easiness of capturing blood cells, as shown in FIG. 4, the V shape whose depth increases toward the central portion of the bottom is preferable. Further, for the collection part 16A, the overflow channel 18A and the flow channel 20A, because a manufacturing method described below is made easy, the rectangle (square, oblong) is preferable.

A volume of the fluid storage 24 is preferably in the range from 5 to 5000 $mm^3$. By setting the volume as described above, each of phenomena which take place in the microchannel can be easily controlled. Horizontal sizes of the substrate 12 and the cover plate 22 are not especially restricted, and may be a size suitable for carrying, for example, 80×50 mm, considering easy usage on site of the blood plasma collection tool 10. Also, thicknesses of the substrate 12 and the cover plate 22 are not especially restricted, and may be, for example, approximately 5 mm, respectively, considering strength, economy, and the like.

Material of the substrate 12 is not especially restricted, but because a manufacturing method described below is made easy, resin material, more specifically, polydimethyl sulfoxide (PDMS), polymethyl methacrylate (PMMA), polyvinyl chloride (PVC), ultraviolet curing resin, polycarbonate (PC) etc. may be preferably used.

Material of the cover plate 22 is not especially restricted, but because of visibility for recognizing phenomena in the flow channel, it may be preferably transparent. As such material, various resin boards, more specifically, polydimethyl sulfoxide (PDMS), polymethyl methacrylate (PMMA), polyvinyl chloride (PVC), ultraviolet curing resin, polycarbonate (PC) etc., various resin films, more specifically, polyethylene terephthalate (PET), polyethylene naphthalate (PEN), triacetyl cellulose (TAC) etc., and various glass (soda-lime glass, borosilicate glass etc.) may be used.

It is preferable that the surface of the substrate 12 (the surface on which the long groove is formed) and the bottom surface of the cover plate 22 (the surface which adheres to the substrate 12) keep sufficient flatness for prevention of fluid leakage.

In order to manufacture the substrate 12 having the fine flow channel described above, the fine processing technology may be suitably used. As the fine processing technology, there are, for example, the following technologies.

(1) LIGA technology having a combination of X-ray lithography and electroplating
(2) High-aspect-ratio photolithography using EPON SU8
(3) Mechanical micro-cutting (micro drilling in which a drill having a drill diameter of a micro order is rotated at a high speed)
(4) High-aspect-ratio processing of silicon by Deep RIE
(5) Hot Emboss processing
(6) Laser beam lithography
(7) Laser beam machining
(8) Ion beam processing Next, a method for firmly attaching the cover plate 22 to the substrate 12 will be described.

First, the substrate 12 and the cover plate 22 are cleaned and subsequently dried. Next, laminating the substrate 12 and the cover plate 22, and they are firmly attached to each other. As for this method for firmly attaching, when material of the substrate 12 and the cover plate 22 is thermoplastic resin, while a laminated body of the substrate 12 and the cover plate 22 is heated to a temperature equal to or higher than their glass transition point Tg, they can be pressurized to be firmly attached to each other. As another method, they can be attached using various adhesives. Further, the operation is preferably conducted in a clean bench or a clean room with cleanliness class being not greater than 100 in view of quality of the blood plasma collection tool 10.

A preferable method for supplying blood into the fluid storage 24 is a method in which blood is supplied by directly touching the fluid storage 24 with a finger tip having blood spilled. Further, there may be a method in which, covering the fluid storage 24 with tape, air expansion caused by pushing down to bend the tape with a finger or heating is used to send fluid. Moreover, there may be also a method for sending fluid using decompression inside the collection part 16A caused by cooling the collection part 16A with ice etc.

Next, procedures for a blood plasma collection method using the blood plasma collection tool 10 according to the present invention will be described with reference to FIGS. 1A and 1B, FIGS. 5A to 5D and FIGS. 6A and 6B. FIGS. 5A to 5D are cross-sectional views illustrating time-series procedures for the blood plasma collection method of the present invention. FIG. 6A is a partial, enlarged cross-sectional view of FIG. 5C, and FIG. 6B is a partial, enlarged cross-sectional view of FIG. 5D.

Figure 5A:
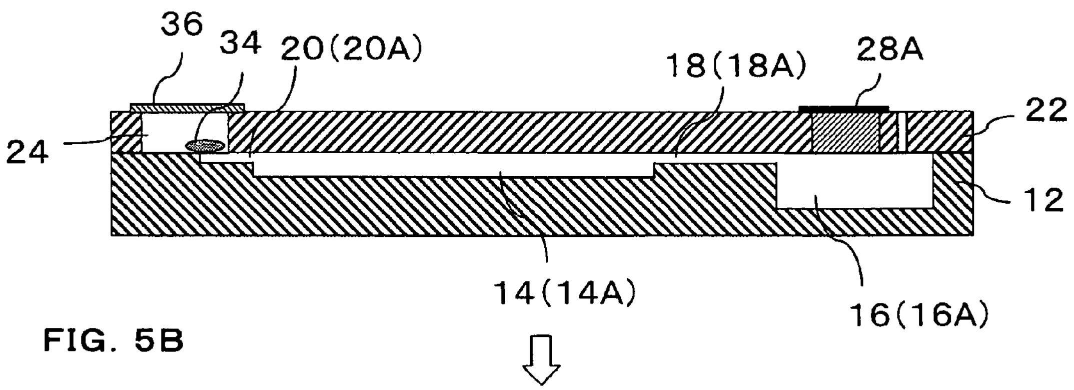
FIGS. 5A to 5D are cross-sectional views illustrating time-series procedures for a blood plasma collection method of the present invention.
Figure 6A:
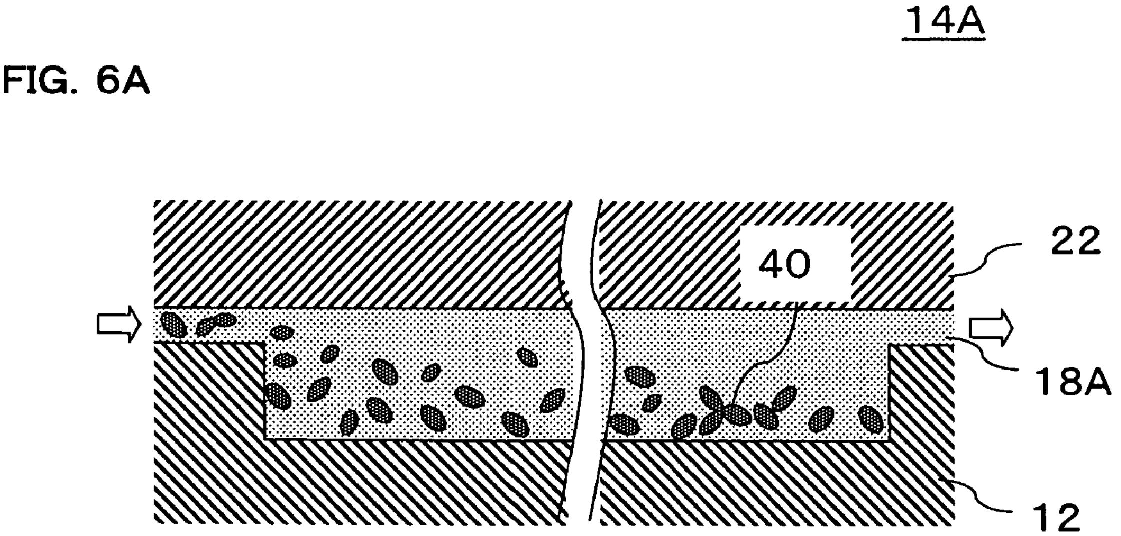
FIGS. 6A and 6B are partial, enlarged cross-sectional views of FIGS. 5A to 5D.
Figure 6B:
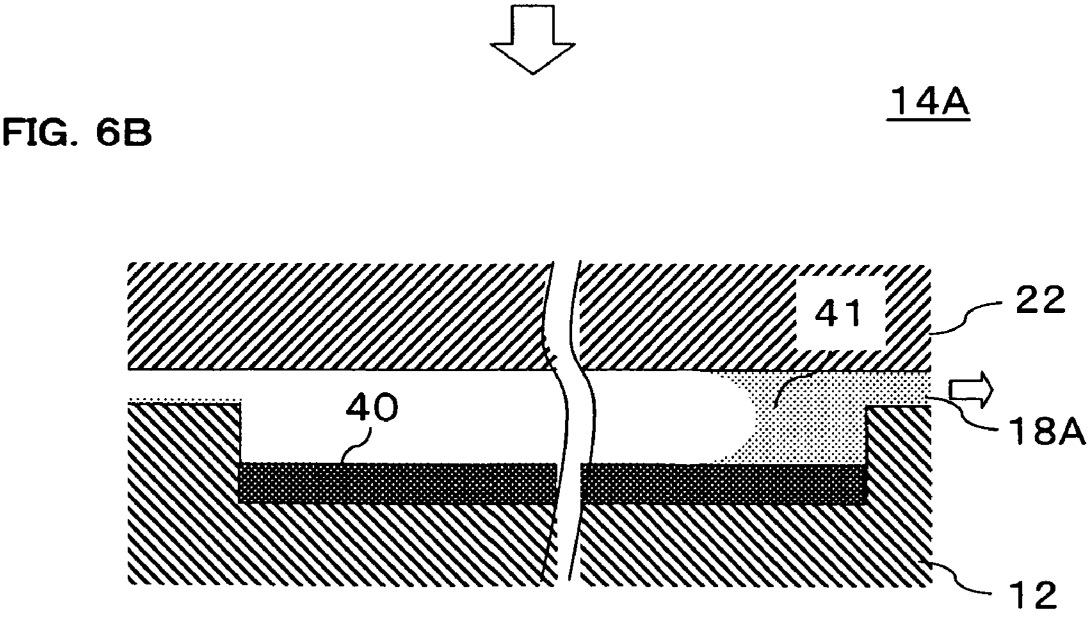

As shown in FIG. 5A, a predetermined amount of blood 34 is supplied to the fluid storage 24 by directly touching the fluid storage 24 with a finger tip having blood spilled. This blood 34, as shown in FIG. 5A, is supplied so as to block a portion in communication with the flow channel 20A in the fluid storage 24. Subsequently, the fluid storage 24 is covered with sealing tape 36. This tape 36 has adhesive coat on its one surface (back surface in the figures), and accordingly the fluid storage 24 is isolated from the outside air. By the way, an amount of blood supplied is the amount allowed to be collected by a lancet, that is, preferably an amount of 1 μL or more to 50 μL or less, and more preferably an amount of 1 μL or more to 10 μL or less. A supply flow rate of blood Q from the fluid storage 24 is set so that the amount of blood supplied can pass through the separation part 14A within 10 min equal to a separation time by centrifugal separation, and preferably not smaller than 0.1 μL/min and not greater than 5 μL/min.

Figure 5B:
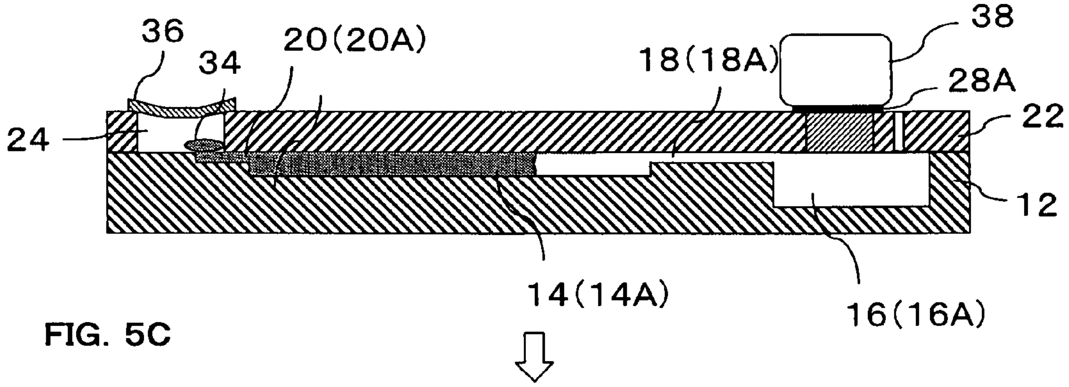
Figure 5C:
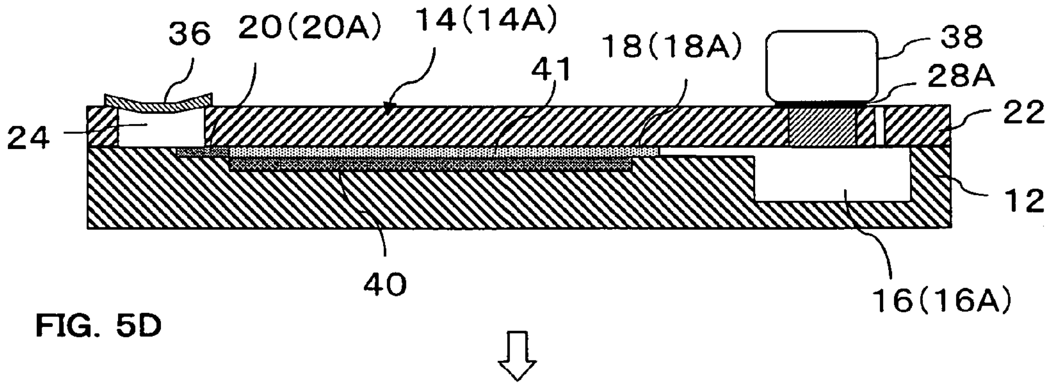

Next, as shown in FIG. 5B, the collection part 16A is sealed with a cover member 28A and ice 38 is placed on an upper portion of the cover member 28A or around it. Accordingly, the inside of the collection part 16A is decompressed, and thereby the blood 34 is sent from the fluid storage 24 into the separation part 14A. In order to more decompress the inside of the collection part 16A, it is preferable to seal suitably the air vent 30 with a seal etc.

Further, as shown in FIG. 5C, in process that the blood 34 flows in the separation part 14A, the blood cell 40 in the blood 34 begins to spontaneously precipitate. The blood cell 40 which precipitated is laminated on the bottom of the separation part 14A and blood plasma 41 from which the blood cells are separated flows into the overflow channel 18A as the supernatant fluid (see FIGS. 6A, 6B).

Figure 5D:
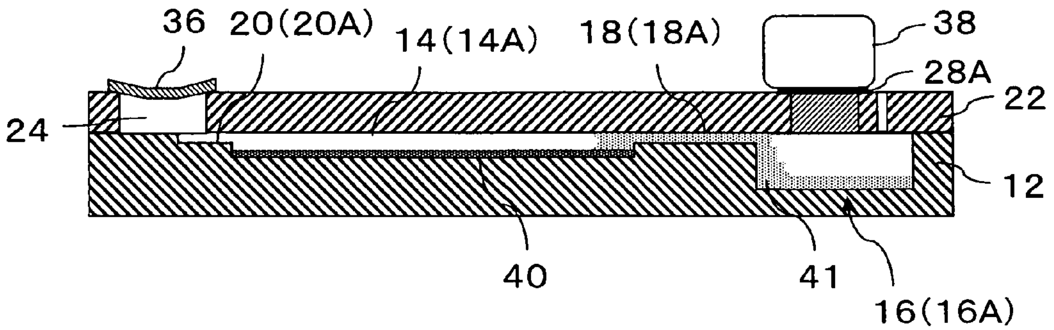

As shown in FIG. 5D, the blood plasma 41 from which the blood cells are separated in the separation part 14A, after flowing in the overflow channel 18A, is introduced into the collection part 16A. Accordingly, only the blood plasma 41 can be collected in the collection part 16A.

The collected blood plasma 41 is collected externally by a syringe not shown etc. through the collection port 28, and subsequently processed by various analysis and/or inspection equipment.

As described above, using the phenomenon of spontaneous sedimentation of blood cells in blood due to an effect of gravitational force which takes place in the very narrow microspace having the depth in the direction of gravitational force of not greater than 1 mm, blood plasma can be collected by accurately, readily separating blood plasma and blood cells in the small amount of blood from each other in a short time. Further, the separation of blood plasma and blood cells can be conducted by the small tool having a simple structure.

As mentioned above, the preferred embodiments of the blood plasma collection method and tool according to the present invention have been described, but the present invention is not limited to the embodiments described above, and various aspects may be made thereto.

For example, in this embodiment, the width W of the overflow channel 18A in the horizontal direction is made smaller than those of the separation part 14A and the collection part 16A, but not limited to this, the width may be made equal to that of the separation part 14A, and also may be reduced gradually from the upstream side (on the side of the separation part 14A) toward the downstream side (on the side of the collection part 16A). The diameter of the flow channel 20A is not especially limited to the aspect of FIGS. 1A and 1B either.

Further, in this embodiment, the blood plasma collection tool for separating blood cells from blood to collect blood plasma has been described, but not limited to this, and it may be used as analysis and/or inspection instrument. For example, a diagnostic reagent is applied on an inner wall face of the collection part 16A (the bottom surface etc.) or put into there, and also blood plasma can be introduced into the collection part 16A to be analyzed or inspected on site. In this case, a substrate 12 and a cover plate 22 constituting a blood plasma collection tool 10 are formed of transparent material. Further, in order to observe more easily a phenomenon, a magnifying glass function (lens function) may be provided on the cover plate 22 corresponding to a portion of the collection part 16A. Moreover, when a blood plasma collection tool is used disposably, the collection port 28 may not be necessarily provided.

Figure 7:
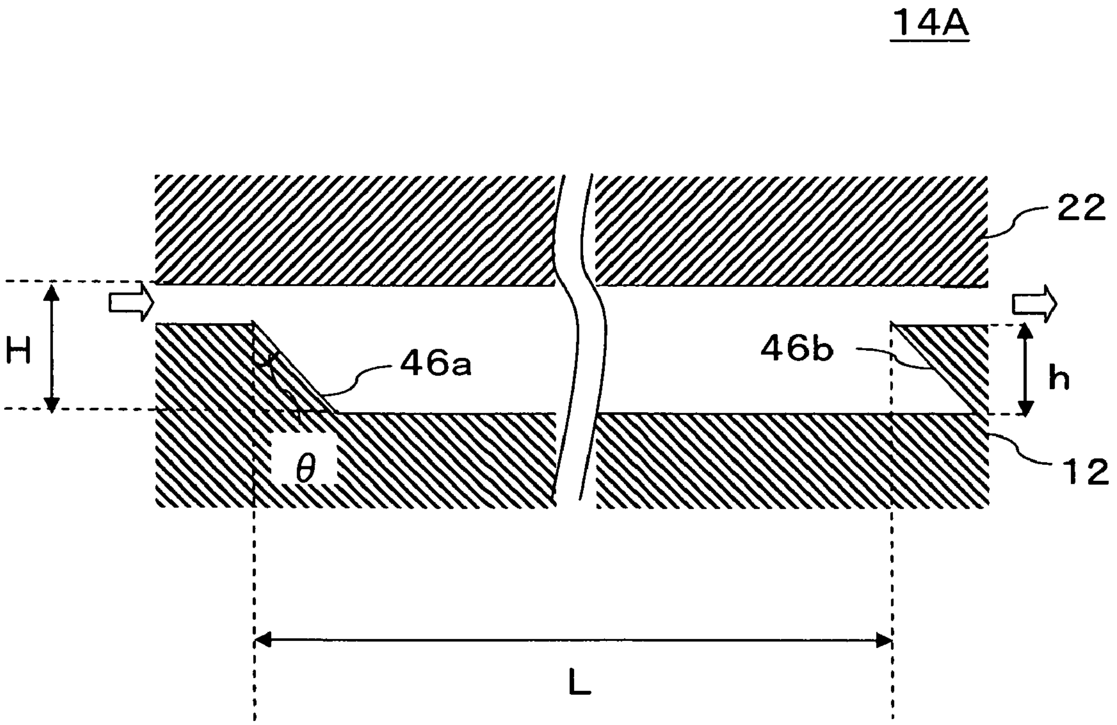
FIG. 7 is a view of a variation of the separation part.

Further, in this embodiment, the cross section shape of the separation part 14A taken along the line A-A is not limited to the shape of FIG. 2, but it may be configured as shown in FIG. 7. That is, in FIG. 7, a side wall face 46*a* of the separation part 14A on the side of the inlet and a side wall face 46*b* of the separation part 14A on the side of the outlet are inclined toward the side of the inlet relative to the direction of gravitational force. This inclined angle θ may be arbitrarily set in the range smaller than 90°. According to the aspect of FIG. 7, the following boycott effect is generated. That is, blood cells precipitate in the direction of gravitational force in the separation part 14A, and on the one hand, blood plasma goes up along the side wall face 46*b* of the separation part 14A on the side of the outlet. As the result, in the separation part 14A, an annular flow of blood plasma is formed, in which an upward flow which went up along the side wall face 46*b* of the separation part 14A on the side of the outlet goes down along the side wall face 46*a* of the separation part 14A on the side of the inlet as a downward flow. Accordingly, sedimentation of blood cells and the upward flow of blood plasma do not collide head-on, and therefore it is enabled to rapidly separate blood plasma and blood cells from each other in a short time. Further, a flow in the direction opposite to the direction of blood flow is generated in boundaries between the separation part 14A and the overflow channel 18A, whereby blood cells can be prevented from entering the overflow channel 18A. In addition, FIG. 7 shows an example that both of the side wall faces 46*a*, 46*b* of the separation part 14A are inclined toward the inlet, but not limited to this, the side wall faces 46*a*, 46*b* of the separation part 14A may be inclined toward the outlet. In this case, also the inclined angle relative to the direction of gravitational force may be arbitrarily set in the range smaller than 90°.

Figure 8:
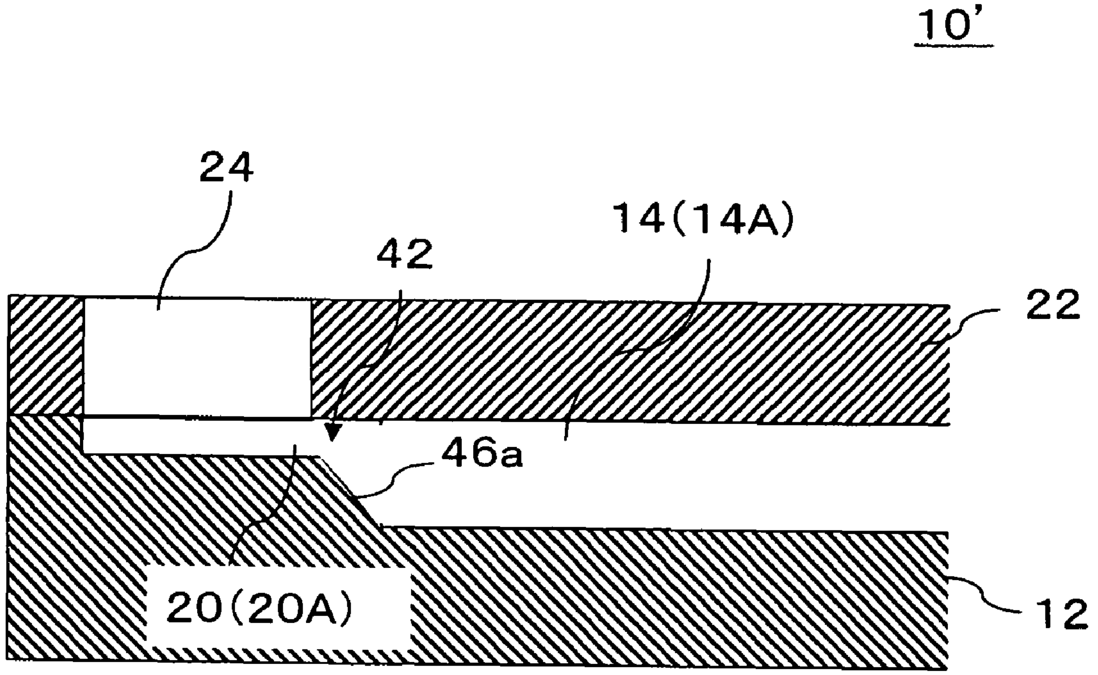
FIG. 8 is a view of a variation of an inlet of the separation part.

FIG. 8 is a partial, cross-sectional view of a variation of a shape of an inlet 42 of the separation part 14A. As shown in FIG. 8, the inlet 42 may be formed by inclining only the side wall face 46*a* of the separation part 14A on the side of the entrance. This inclined angle may be set similarly to the case of FIG. 7 as described above. In addition, not limited to the aspect of FIG. 8, the side wall face 46*a* of the separation part 14A may be inclined toward the outlet. Accordingly, blood cells can be captured effectively.

Figure 9:
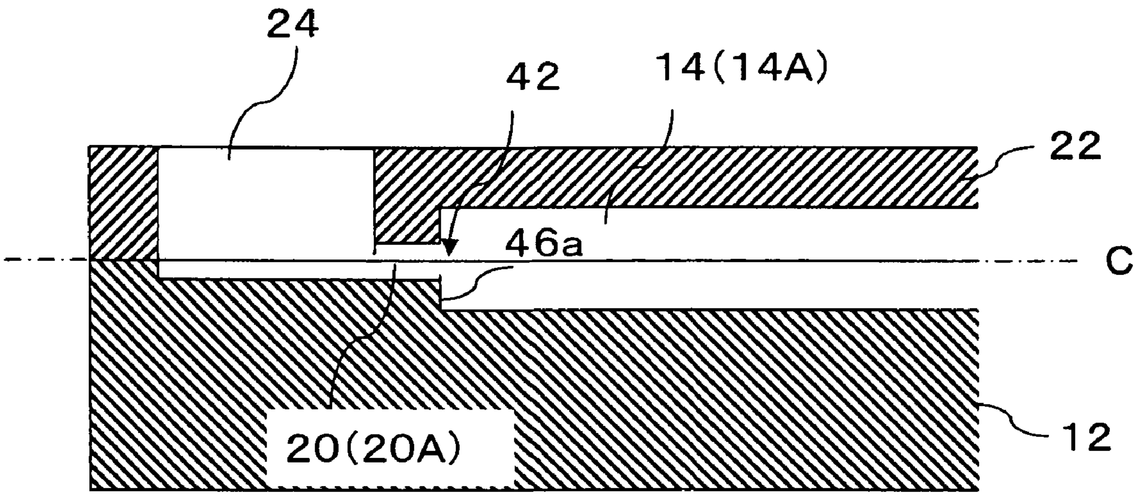
FIG. 9 is a view of a variation of the inlet of the separation part.

Further, a position of the inlet 42 of the separation part 14A is not limited to the aspect of FIG. 2, but it may be configured as shown in FIG. 9. FIG. 9 is a partial, cross-sectional view of a variation of the position of the inlet 42 of the separation part 14A. As shown in FIG. 9, the inlet 42 may be formed at the middle of the depth H of the side wall face of the separation part 14A in the direction of gravitational force (the center of the inlet 42 is positioned on the center line C). Accordingly, a distance between an interface of blood introduced into the separation part 14A and an upper surface of the separation part 14A becomes equal to a distance between the interface and a bottom surface of the separation part 14A, and thereby blood can be prevented from covering only any one of the surfaces and spreading.

Figures 10A, 10B:
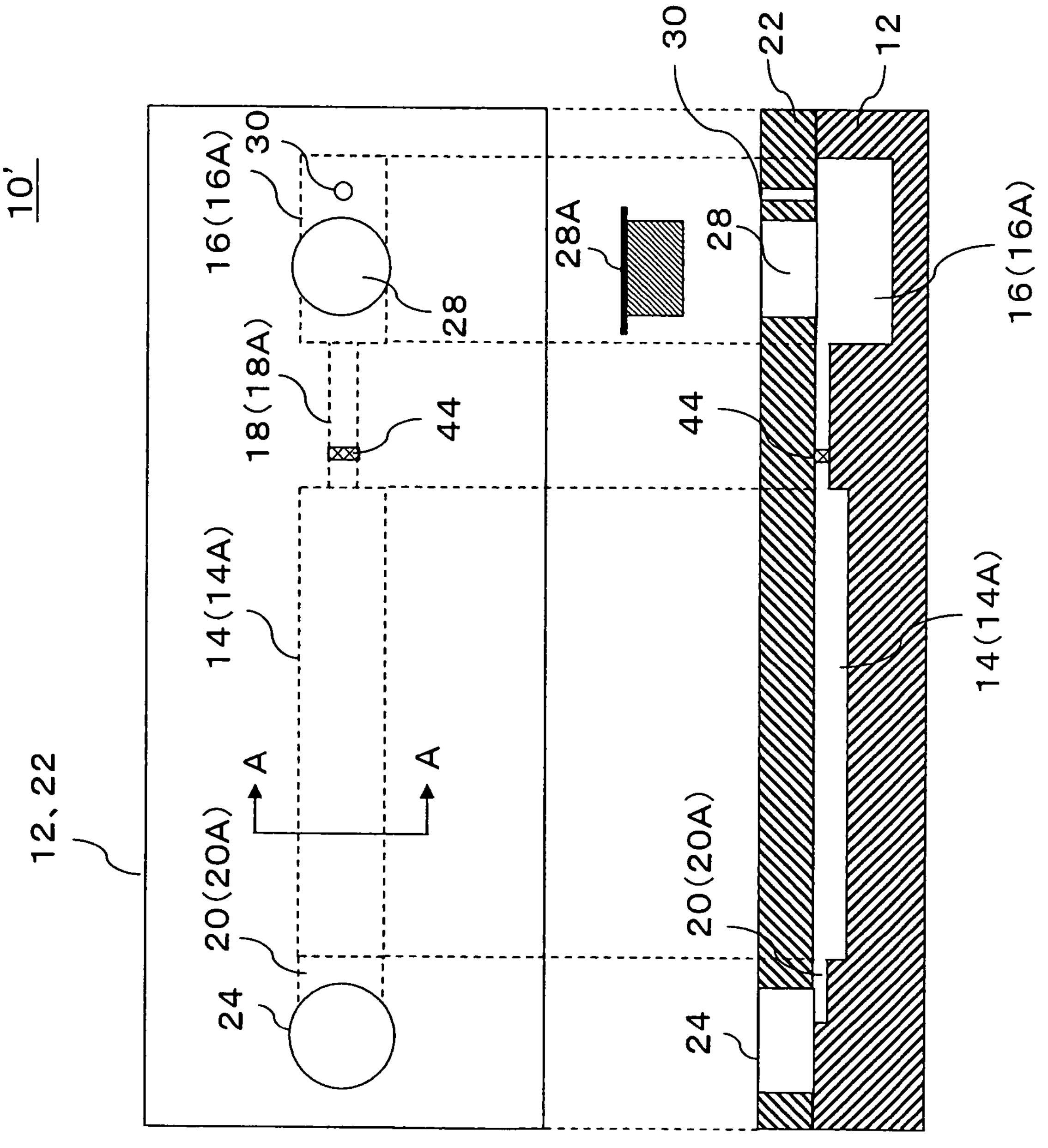
FIGS. 10A and 10B are views for describing a variation of the blood plasma collection tool.

Further, one or more filters or dams may be provided in the overflow channel 18A for communicating the separation part 14A with the collection part 16A. FIGS. 10A and 10B are views illustrating a blood plasma collection tool 10' in which a filter 44 is provided in the overflow channel 18A. According to the aspect of FIGS. 10A and 10B, blood cells which could not be separated out in the separation part 14A can be further captured in the overflow channel 18A, whereby blood plasma can be accurately collected in the collection part 16A. Further, blood plasma after blood cells are separated out in the separation part 14A is passed through the filter 44, and therefore it is difficult for the filter 44 to be clogged, whereby necessity of frequent replacement of the filter is eliminated. In addition, an installation location of the filter 44 in the overflow channel 18A and the number of installation are not limited to the aspect of FIGS. 10A and 10B. Further, a combination of the dam and the filter may be also installed in the overflow channel 18A.

Figures 11A, 11B:
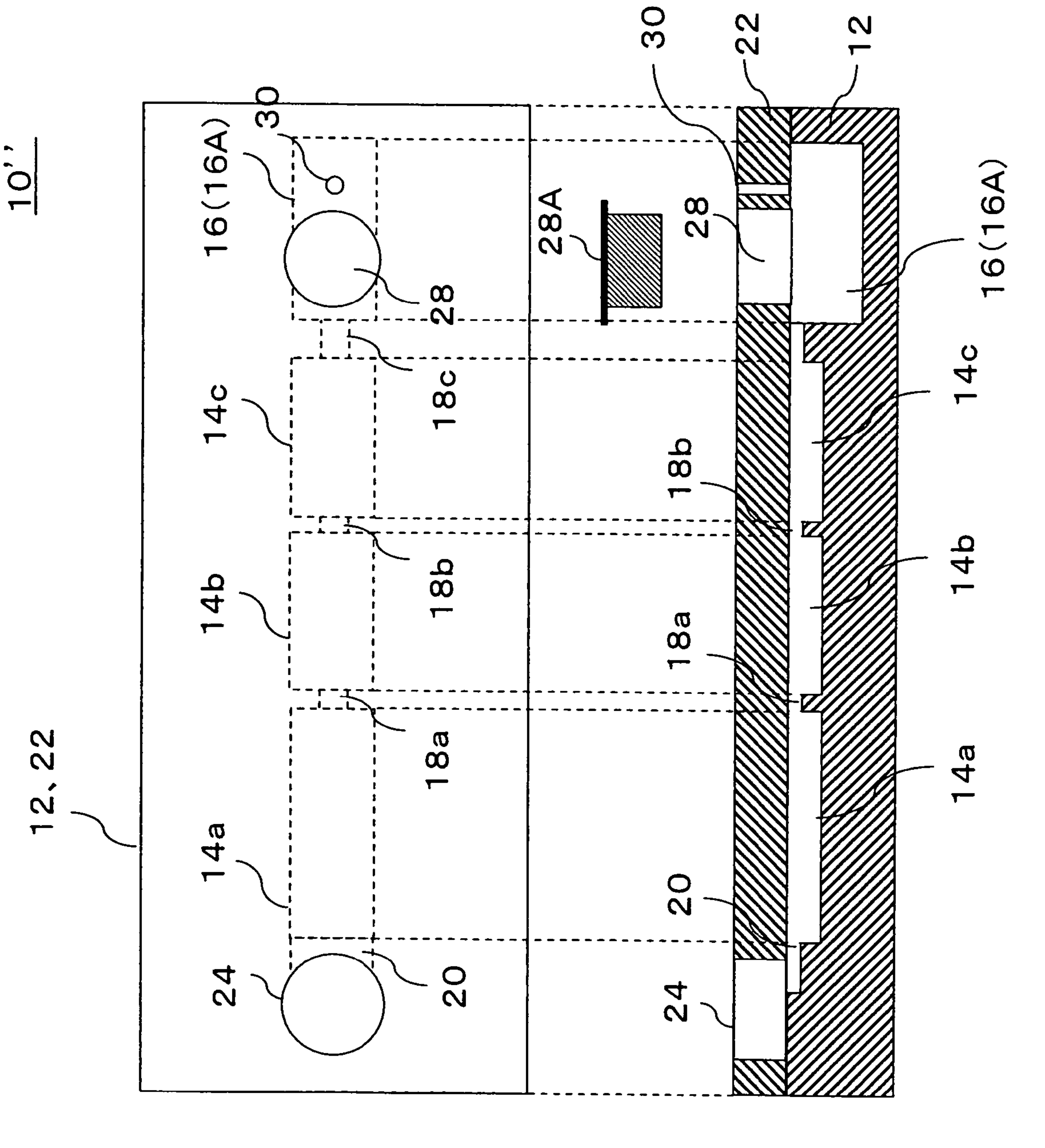
FIGS. 11A and 11B are views for describing a variation of the blood plasma collection tool.

Further, in this embodiment, an example that only one separation part 14A is provided has been shown, but not limited to this, as shown in FIGS. 11A and 11B, a plurality of the separation parts 14A may be provided. FIGS. 11A and 11B are schematic views illustrating a blood plasma collection tool 10" in which a plurality of separation parts 14*a*, 14*b*, 14*c* are provided in series. In the aspect of FIGS. 11A and 11B, each of the separation parts 14*a* to 14*c* is communicated with each other by a plurality of overflow channels 18*a* to 18*c*. Accordingly, blood cells which could not be separated out in the separation part 14*a* can be separated out in steps in the separation parts 14*b*, 14*c*, whereby blood plasma having few contamination of blood cells can be collected. In addition, the number of installation of the separation part is not limited to the aspect of FIGS. 11A and 11B, but the number may be even two, or four or more.

EXAMPLES

An experiment on collection of blood plasma was conducted using the blood plasma collection tool 10 shown in FIGS. 1A and 1B. The blood plasma collection tool 10 used had the depth H of the separation part 14A in the direction of gravitational force of 0.2 mm, the width W of 1 mm, the length L in the flow direction of 25 mm, the height h of the overflow channel 18A of 0.02 mm, and the volume of the separation part 14A of 5 μL.

Among cell components in blood, most of them are red blood cells (in blood of 1 μL, the number of red blood cells is approximately five million, the number of leukocytes is in the range from 5000 to 10000, and the number of blood platelets is two hundred fifty thousand). Therefore, the separation part 14A was designed, selecting red blood cells as target blood cells to be separated out, and considering the sedimentation time of red blood cells.

Supposing that a diameter of blood cells is 5.7 μm, approximating by a sphere, the spontaneous sedimentation rate vb of red blood cells was 1.6 μm/sec obtained from the expression (1). For fluid characteristics of blood, $\rho 1=1.09$ g/cm$^3$, $\rho 2=1.0$ g/cm$^3$, and $\eta=0.01$ poise were used, and the calculation was made with each of these characteristic values being converted to be expressed in suitable units described above.

Example 1

Blood of 5 μL all was dropped into the fluid storage 24 (diameter: 3 mm, depth: 2 mm) formed in the blood plasma collection tool 10. The fluid storage 24 was covered by applying a thin tape 36 on it and ice was placed on the cover plate 22 on the side of blood plasma collection. Due to this ice, a gas in the collection part 16A was cooled to contract in volume, supplying the blood to the flow channel 20A, the separation part 14A, the overflow channel 18A and the collection part 16A.

At this time, the maximum supply flow rate of blood was 2.4 μL/min. Further, the initial rate vo in the horizontal direction in the separation part 14A was 12 mm/min, and a retention time of blood in the separation part 14A was 2 min.

Reynolds number Re in the separation part 14A was 0.07, which was obtained as the result of calculation using a circle equivalent diameter of the separation part 14A $D=4\times1\times0.2/2\times(1+0.2)=0.33$ mm and fluid characteristics of blood plasma having a low viscosity ($\rho=1.0$ g/cm$^3$ and $\eta=0.01$ poise), and it was confirmed that a laminar flow was formed. Operation of the blood plasma collection tool 10 ended when the blood plasma reached the collection part 16A.

As the result, the blood cells dropped to 200 μm at a maximum, and could be collected in the separation part 14A. Further, the blood plasma collected in the collection part 16A was visually observed by a microscope to measure a contamination rate of red blood cells, and as the result, the contamination rate of red blood cells was 0%.

Example 2

Next, an experiment was made similarly to the example 1, except that the supply flow rate of blood was increased to 5 μL/min and the height h of the overflow channel 18A was changed to 105 μm.

At this time, when the initial rate vo in the separation part 14A was 25 mm/min and the retention time of blood in the separation part 14A was t=L/vo=1 min, then the sedimentation distance Hb of blood cells was 96 μm. Further, Reynolds number Re in the separation part 14A was 0.14 and the laminar flow was formed. Operation of the blood plasma collection tool 10 ended when the blood plasma reached the collection part 16A.

As the result, blood cells could be separated out in the separation part 14A and blood plasma could be collected in the collection part 16A. Further, the blood plasma collected in the collection part 16A was visually observed by a microscope to measure the contamination rate of red blood cells, and as the result, the contamination rate of red blood cells was 0%.

Comparative Example 1

Next, an experiment was made similarly to the example 2, except that the height h of the overflow channel 18A was changed to 20 μm.

As the result, in the blood plasma collection tool 10, blood cells entered the collection part 16A and then blood plasma by itself could not be collected. At this time, when the initial rate vo in the separation part 14A was 25 mm/min and the retention time of blood in the separation part 14A was t=L/vo=1 min, then the sedimentation distance Hb of blood cells was 96 μm. Therefore, blood cells which reached the side wall face 46*b* of the separation part 14A on the downstream side was situated at a position of 104 μm from the bottom of the separation part 14A, and on the contrary, the height h of the overflow channel 18A was 20 μm, so that it was thought that the blood cells flowed into the collection part 16A through the overflow channel 18A.

As mentioned above, it was found that, using the blood plasma collection method and tool according to the present invention, blood plasma could be separated from blood in a short time.

What is claimed is:

1. A blood plasma collection tool, comprising:

a separation part for separating blood cells from blood due to spontaneous sedimentation;

a collection part for collecting blood plasma obtained by separation of blood cells in the separation part as supernatant fluid; and an overflow channel for overflowing the blood plasma separated out in the separation part to the collection part, wherein the separation part is a long microspace having an upper planar surface and a lower planar surface, wherein a distance between the upper planar surface and the lower planar surface is not greater than 1 mm, wherein said separation part has an inlet side face and an outlet side face, said inlet side face and outlet side face facing each other across the long microspace, wherein one of said inlet side face and said outlet side has an angle of inclination to form a ramp with the lower planar surface and the other of said inlet side face and said outlet side face has an inclined face.

2. The blood plasma collection tool according to claim 1, wherein

H (m) is a distance between the upper planar surface and the lower planar surface of the separation part, L (m) is a length of the separation part in the flow direction of the blood and Hb (m) is a sedimentation distance in which the blood cells can precipitate while the blood passes through the length (L) of the separation part, then it is the condition that a height h (m) of a bottom surface of the overflow channel relative to the bottom planar surface of the separation part satisfies either (A) or (B):

(A) when $Hb \geqq H$, $h \geqq 2\times10^{-5}$ m (B) when $Hb<H$, $h \geqq H-Hb$ m.

3. The blood plasma collection tool according to claim 1, wherein a dam is provided in the overflow channel.

4. The blood plasma collection tool according to claim 2, wherein a dam is provided in the overflow channel.

5. The blood plasma collection tool according to claim 1, wherein a filter is provided in the overflow channel.

6. The blood plasma collection tool according to claim 2, wherein a filter is provided in the overflow channel.

7. The blood plasma collection tool according to claim 1, wherein a plurality of separation parts are provided in series.

8. The blood plasma collection tool according to claim 2, wherein a plurality of separation parts are provided in series.

9. The blood plasma collection tool according to claim 1, wherein an inlet of the separation part is formed in a central part of a side wall face of the separation part, said side wall disposed between the upper and lower planar surfaces.

10. The blood plasma collection tool according to claim 2, wherein an inlet of the separation part is formed in a central part of a side wall face of the separation part, said side wall disposed between the upper and lower planar surfaces.

11. The blood plasma collection tool according to claim 1, wherein a cross section shape of a bottom of the separation part on a cross section in the width direction of the blood flow is of V-shaped type whose depth increases from both ends toward the central portion.

12. The blood plasma collection tool according to claim 2, wherein a cross section shape of a bottom of the separation part on a cross section in the width direction of the blood flow is of V-shaped type whose depth increases from both ends toward the central portion.

13. The collection tool of claim 1, wherein said separation part includes an inlet port and an outlet port, wherein the inlet port and outlet port are disposed on opposite ends of the long microspace and are formed in walls other than the upper planar surface and the lower planar surface.

14. The collection tool of claim 13, wherein said inlet side face has the angle of inclination to form the ramp with the lower planar surface, and the inclined face of the outlet side face is disposed to be oriented more towards the lower planar surface and less towards the upper planar surface to provide a boycott effect of blood cells.

15. The collection tool of claim 13, wherein said outlet side face has the angle of inclination to form the ramp with the lower planar surface, and the inclined face of the inlet side face is disposed to be oriented more towards the lower planar surface and less towards the upper planar surface to provide a boycott effect of blood cells.

16. The collection tool of claim 14 wherein the angle of inclination of the inlet side face is smaller than 90° as measured from a normal reference line to the lower planar surface, and the inclined face of the outlet side face is substantially parallel to the ramp of the inlet side face.

17. The collection tool of claim 15 wherein the angle of inclination of the outlet side face is smaller than 90° as measured from a normal reference line to the lower planar surface, and the inclined face of the inlet side face is substantially parallel with the ramp of the outlet side face.

* * * * *